United States Patent
Nakanishi

(10) Patent No.: US 6,784,271 B2
(45) Date of Patent: Aug. 31, 2004

(54) ODORLESS MODIFIED SILICONE COMPOUND, COSMETIC PREPARATION CONTAINING THE SAME, AND METHOD OF PURIFYING MODIFIED SILICONE COMPOUND HAVING BRANCH POLYMER COMPRISING HYDROPHILIC GROUP

(75) Inventor: Tetsuo Nakanishi, Gunma (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 5 days.

(21) Appl. No.: 10/221,274

(22) PCT Filed: Jan. 10, 2002

(86) PCT No.: PCT/JP02/00066

§ 371 (c)(1),
(2), (4) Date: Sep. 10, 2002

(87) PCT Pub. No.: WO02/055588

PCT Pub. Date: Jul. 18, 2002

(65) Prior Publication Data

US 2003/0158363 A1 Aug. 21, 2003

(30) Foreign Application Priority Data

Jan. 10, 2001 (JP) .......................................... 2001-2558

(51) Int. Cl.$^7$ ............................................. C08G 77/12
(52) U.S. Cl. ............................. 528/25; 528/31; 528/29; 528/499; 556/445; 568/673; 525/474; 524/588
(58) Field of Search ............................. 528/31, 25, 29, 528/499; 556/445; 568/673; 525/474; 524/588

(56) References Cited

U.S. PATENT DOCUMENTS 5,225,509 A  7/1993  Heinrich et al.
5,696,192 A  * 12/1997  Harashima

FOREIGN PATENT DOCUMENTS

| JP | 63-202629 | 8/1988 |
| JP | 2-302438 | 12/1990 |
| JP | 5-186596 | 7/1993 |
| JP | 7-330907 | 12/1995 |
| JP | 9-165315 | 6/1997 |
| JP | 9-165318 | 6/1997 |
| JP | 9-202829 | 8/1997 |
| JP | 2000-327785 | 11/2000 |

* cited by examiner

Primary Examiner—Kuo-Liang Peng
(74) Attorney, Agent, or Firm—Millen White Zelano & Branigan, P.C.

(57) ABSTRACT

A modified silicone compound having a branch polymer comprising a hydrophilic group, this compound being synthesized by performing an addition reaction between an organohydrogenpolysiloxane, and at least one compound chosen from an alkenylated polyoxyalkenylated compound, an alkenylated glycerine compound and an alkenylated sugar in the presence of a platinum catalyst or rhodium catalyst, and a cosmetic material containing this modified silicone compound. This compound is purified by decomposing aldehyde condensation products remaining in the silicone by alkylating the remaining unsaturated bonds after hydrogenating the reaction liquor after said addition reaction, and treating with an aqueous solution of pH 7 or lower containing an acidic substance, or decomposing the propenyl etherated polyether in the reaction liquor after said addition reaction by treating with an aqueous solution of pH 7 or lower containing an acidic substance, and then alkylating the generated aldehydes and alkenylated ether compounds by hydrogenation. The degree of unsaturation (meq/g) in the modified silicone compound is 0.002 or less. The generation amount of aldehydes when heat ageing is performed in 0.23N hydrochloric acid at 50° C. for 0.5 hours is 70 ppm or less of the modified silicone compound.

15 Claims, No Drawings

ODORLESS MODIFIED SILICONE COMPOUND, COSMETIC PREPARATION CONTAINING THE SAME, AND METHOD OF PURIFYING MODIFIED SILICONE COMPOUND HAVING BRANCH POLYMER COMPRISING HYDROPHILIC GROUP

SPECIFICATION

An odorless silicone compound, a method of preparing a cosmetic material containing it, and a modified silicone compound comprising a branch polymer comprising a hydrophilic group.

1. Field of the Invention

This invention relates to a purified, modified silicone compound which has very little odor over time even when blended in an aqueous system, and to a method of manufacturing a cosmetic material containing same and a modified silicone compound comprising a branch polymer comprising a hydrophilic group.

2. Background of the Invention

Conventionally, modified silicone compounds were manufactured by carrying out an addition reaction between a hydrogen siloxane and a compound with a terminal double bond in the presence of a precious metal catalyst such as platinum hydrochloride. However, since an odor was acquired with time when a polyether modified silicone obtained in this way was used in an emulsification system, it was difficult to use in cosmetics.

Describing this mechanism, in a polyether modified silicone compound, the polyether modified silicone will suffer oxidative degradation with time, generating formaldehyde and acetaldehyde.

That is, for example, when an allyl etherated polyether is used as a polyoxyalkylene, when the addition reaction between this and hydrogen siloxane is performed in the presence of a platinum catalyst, the allyl group undergoes an internal shift as a side reaction, generating propenyl etherated polyether. As this propenyl etherated polyether does not react with hydrogen siloxane, it remains as an impurity in the polyether modified silicone produced by the normal addition reaction, and unreacted allyl etherated polyether also remains in the polyether as an impurity. Moreover, it isomerizes gradually due to the remaining platinum catalyst, and unreacted allyl etherated polyether becomes propenyl etherated polyether. Therefore, if water acts on the polyether modified silicone containing these impurities, cleavage of the propenyl ether will occur, generating propionaldehyde and a foul odor. This reaction is promoted by acids, and the reaction velocity increases the lower the pH.

JP App. No. 01-123053, based on the elucidation of the aforesaid second odor-causing mechanism, discloses that under certain conditions, in an aqueous solution of pH 7 or less, an odorous substance was generated by treating a polyether modified silicone containing the above-mentioned impurities until the degree of unsaturated bonds in the residual double bond containing polyether in the polyether modified silicone became 0.002 or less, and when this was removed, the polyether modified silicone no longer caused a foul odor even after time had elapsed.

However, the following problems occur with the above-mentioned acid solution. Specifically, the reaction of hydrogen siloxane and allyl etherated polyether is not always the same. The allyl etherated polyether content which remains, changes when the rate of the addition reaction changes, and the propenyl etherated polyether content also changes. Therefore, the required reaction time and concentration of acid solution differ for every batch. Moreover, there is a difference in the rate of hydrolysis between allyl etherated polyether and propenyl etherated polyether. Under the same reaction conditions, as the hydrolysis rate of allyl etherated polyether is slow, allyl etherated polyether remains, propenyl etherated polyether is produced with time, and substances with a foul odor are generated.

If chlorination is performed under rigorous conditions to hydrolyze the allylated ether, the polyoxyalkylene group is oxidized and a foul odor is again produced.

As a means to solve the batch difference due to the reaction rate, U.S. Pat. No. 5,225,509 and JP 7-330907 disclose a method of hydrogenating the unsaturated double bonds by a hydrogen addition reaction. This method is not based on the difference between allyl dietherated polyether and propenyl etherated polyether, and may be expected to permit hydrogenation of the unsaturated double bonds so that the generation of propionaldehyde can be stably controlled.

However, when this researcher carried out studies to manufacture a more stable modified silicone, he discovered that with a hydrogen addition reaction alone, aldehyde condensation products such as acetal, paraldehyde and aldole remain, producing aldehyde in solution and causing a foul odor. As these compounds do not have unsaturated bonds in the molecule, they cannot be removed at all by the hydrogen addition reaction. Moreover, as they do not have unsaturated bonds, it is ineffectual to control the degree of unsaturation.

The generation of a foul odor by such aldehyde condensation products was not disclosed by either of the above patents, their chief aim being focused on treating the unreacted, unsaturated groups containing polyether.

The inventors found that by performing hydrogen addition processing on a modified silicone having a hydrophilic group as branch polymer, and carrying out the reaction at pH 7 or less, the foul odor due to aldehyde condensation products of this modified silicone can be prevented, and they thereby arrived at the present invention.

It is therefore a first object of this invention to provide a modified silicone which has a hydrophilic group as branch polymer, and which does not produce a foul odor with time.

It is a second object of this invention to provide a cosmetic material which uses a modified silicone having a hydrophilic group as branch polymer, and which does not produce a foul odor with time.

It is a third object of this invention to provide a method of purifying the modified silicone having a hydrophilic group as branch polymer.

DISCLOSURE OF THE INVENTION

This invention is related to a modified silicone compound having a branch polymer comprising a hydrophilic group synthesized by an addition reaction of an organohydrogen polysiloxane and at least one type of compound chosen from an alkenylated polyoxyalkylene compound, alkenylated glycerine compound and alkenylated sugar in the presence of a platinum catalyst or rhodium catalyst, and which contains a hydrophilic group. In this compound, unsaturated bonds which remain after performing a hydrogen addition reaction on the reaction solution after the above-mentioned addition reaction, are hydrogenated. Subsequently, aldehyde condensation products which remain in the silicone are decomposed by treating with an aqueous solution of pH 7 or less containing an acidic substance as reagent, or they can be decomposed by treating the propenyl etherated polyether in the reaction solution after the above addition reaction, using an aqueous solution of pH 7 or less containing an acidic substance as reagent. Then, the above-mentioned modified silicone compound is purified by hydrogenated the aldehyde and the alkenylated ether compound purified by the hydrogen addition reaction. The odorless modified silicone compound, and the cosmetic materials prepared from it, are characterized in that the degree (meq/g) of unsaturation of this modified silicone compound is 0.002 or less overall, and the amount of aldehyde produced by heat aging at 50° C. for 0.5 hours in 0.23N hydrochloric acid is 70 ppm or less.

The modified silicone compound which comprises an organopolysiloxane having a branch polymer comprising the above-mentioned hydrophilic group, is represented by the following general formula (1):

$$R^1_a R^2_b SiO_{(4-a-b)/2} \tag{1}$$

In the above formula, $R^1$ are identical or different organic groups chosen from an alkyl group with 1–30 carbon atoms, an aryl group, an aralkyl group, a fluorosubstituted alkyl group or an organic group represented by the general formula (2):

$$—C_m H_{2m}—O—(C_2 H_4 O)_c (C_3 H_6 O)_d R^3 \tag{2}$$

where $R^3$ is a hydrocarbon group having 5–30 carbon atoms, or an organic group represented by $R^4$—(CO)— (in the formula, $R^4$ is a hydrocarbon group with 1–30 carbon atoms.)
c, d, and m are integers in the range $0 \leq c \leq 50$, $0 \leq d \leq 50$ and $0 \leq m \leq 15$, respectively. $R^2$ is a hydrophilic group represented by the following general formula (3).

$$—Q—O—X \tag{3}$$

(in the formula, Q is a divalent hydrocarbon group with 3–20 carbon atoms which may contain at least one of an ether bond or ester bond, and X is a monovalent hydrophilic group chosen from polyoxyalkylene, glycerin, and sugar). a and b are given by $1.0 \leq a \leq 2.5$ and $0.001 \leq b \leq 1.5$, respectively.

DESCRIPTION OF THE PREFERRED EMBODIMENTS

The modified silicone compound of this invention comprises an organopolysiloxane having a branch polymer comprising a hydrophilic group, and may be specifically represented by the following general formula (1).

$$R^1_a R^2_b SiO_{(4-a-b)/2} \tag{1}$$

In the formula, $R^1$ are identical or different organic groups chosen from an alkyl group having 1–30 carbon atoms, an aryl group, an aralkyl group and a fluorosubstituted alkyl group. Specific examples of alkyl groups are methyl, ethyl, propyl, butyl, pentyl, hexyl, heptyl, octyl, nonyl and decyl, cycloalkyl groups such as cyclopentyl and cyclohexyl, aryl groups such as phenyl or tolyl, aralkyl groups such as benzyl or phenetyl, or fluoroalkyl groups such as trifluoropropyl or heptadecafluorodecyl. a is an integer in the range $1.0 \leq a \leq 2.5$, and b is an integer in the range $0.001 \leq b \leq 1.5$.

In the formula, $R^1$ may be an organic group containing a long chain alkyl group, represented by the following general formula (2).

$$—C_m H_{2m}—O—(C_2 H_4 O)_c (C_3 H_6 O)_d R^3 \tag{2}$$

In the formula, $R^3$ is an organic group represented by a monovalent hydrocarbon group with 5–30 carbon atoms, or $R^4$—(CO)—. $R^4$ is a hydrocarbon group with 1–30 carbon atoms, c and d are represented by integers in the range 0–50, and m is represented by an integer in the range 0–15, respectively.

Specifically, $R^1$ is an alkoxy group, ester group, alkenyl ether residue or an alkenyl ester residue.

Here, when m is 0, the compound is not easily hydrolyzed regardless of c and d, and when m is 15 or higher, the compound has a strong oily odor, therefore, it is desirable that m is in the range 3–11.

As an example, when m is 0, c=0 and d=0, the alkoxy group with 5–30 carbon atoms may be a higher alkoxy group such as oleoxy or stearoxy, or an ester group such as oleic acid, stearic acid and behenylic acid.
m is 1 or more, and when c=0 and d=0, it is particularly desirable that m=3, 5 or 11.

In this case, the group is an allyl ether, pentenyl ether or undecenyl ether residue, such as for example an allyl stearyl ether residue, allyl behenyl ether residue or an undecenyl oleyl ether residue depending on the substituent group $R^3$.

When c or d is not 0, an alkoxy group or an ester group will exist via polyoxyalkylene.
It is preferred that 50% or more, and more preferred that 70% or more of $R^1$ is methyl, but 100% may be methyl.
$R^2$ is a hydrophilic group represented by the following general formula (3):

$$—Q—O—X \tag{3}$$

In the formula, Q is a divalent hydrocarbon group with 3–20 carbon atoms which may contain an ether bond or an ester bond. For example, $—(CH_2)_2—$, $—(CH_2)_3—$, $—CH_2CH(CH_3)CH_2—$, $—(CH_2)_4—$, $—(CH_2)_5—$, $—(CH_2)_6—$, $—(CH_2)_7—$, $(CH_2)_8—$, $—(CH_2)_2—CH(CH_2CH_2CH_3)—$, $CH_2—CH(CH_2CH_3)—$, $—(CH_2)_3—O—(CH_2)_2—$, $—(CH_2)_3—O—(CH_2)_2—O—(CH_2)_2—$, $—(CH_2)_3—O—CH_2CH(CH_3)—$, $—CH_2CH(CH_3)—COO(CH_2)_2—$.

X is a monovalent hydrophilic group comprising polyoxyalkylene, glycerin or sugar.

When X is a monovalent hydrophilic group comprising polyoxyalkylene, $R^2$ is represented by the following general formula (4):

$$—Q—O—(C_2 H_4 O)_e (C_3 H_6 O)_f—R^5 \tag{4}$$

Q in the formula (4) is the same as Q in the formula (3). $R^5$ is a hydrocarbon group with a hydrogen atom or 1–4 carbon atoms.
e is an integer in the range 2–200, but preferably 5–100. f is an integer in the range 0–200, but preferably 0–100. e+f is in the range 3–200, but preferably 5–100.
In order to give sufficient hydrophilicity to obtain an oil-water emulsion, it is desirable that $e/f \geq 1$.

In addition, when the polyoxyalkylene part of the above-mentioned formula (4) comprises both an ethylene oxide unit and a propylene oxide unit, one of a block polymer of both of these units and a random polymer are sufficient.
When X is a monovalent hydrophilic group comprising glycerine, $R^2$ may be the following residue:

(in the formula, Q is the same as Q in formula (3)).
s and t in the formula are integers in the range 1–20.
Some hydroxyl groups in the following groups may be replaced by an alkoxy group or ester group.

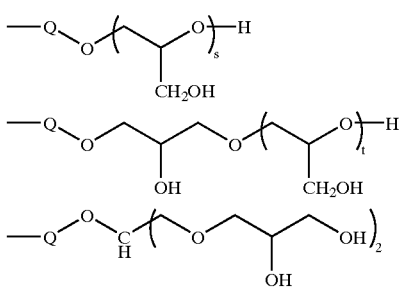

Examples of the sugar residue (X) derived from a monosaccharide, oligosaccharide or polysacccharide, are monosaccharides such as glycosyl, mannosyl, galactosyl, ribosyl, arabinosyl, xylosyl and fructosyl, oligosaccharides such as maltosyl, cellobiosyl, lactosyl, and maltotriosyl, and polysaccharides such as cellulose and starch. Monosaccharides and oligosaccharides are preferred.

a is 1.0–2.5, but preferably 1.2–2.3.

When a is less than 1.0, there is inferior miscibility with oil, and it is difficult to obtain a stable oil-water emulsion.

When a is larger than 2.5, there is inferior hydrophilicity, and it is again difficult to obtain a stable oil-water emulsion.

b is 0.001–1.5, but preferably 0.05–1.0.

When b is less than 0.001, there is inferior hydrophilicity, and it is difficult to obtain a stable oil-water emulsion.

When by is larger than 1.5, hydrophilicity is too high, and it is difficult to obtain a stable oil-water emulsion.

There is no particular limit on the weight average molecular weight of the silicone compound of the above-mentioned formula (1), but when it is used as an emulsifier, it is preferably 500–200,000, and more preferably 1,000–100,000.

When it is used as a skin washing composition, the weight average molecular weight of the silicone compound of the above-mentioned formula (1) is preferably 4,000 or less, more preferably 2,000 or less and still more preferably 1,500 or less.

The silicone compound of the above-mentioned formula (1) used in this invention is easily synthesized by carrying out an addition reaction between an organohydrogen polysiloxane and an alkenylated polyoxyalkylene compound, alkenylated glycerin compound, alkenylated sugar, and if required an alkylenated compound or organic compound represented by the following general formula (5) in the presence of a platinum catalyst or rhodium catalyst.

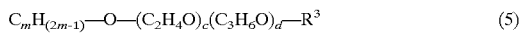

$C_mH_{(2m-1)}$—O—$(C_2H_4O)_c(C_3H_6O)_d$—$R^3$ (5)

The polyoxyalkylene compound may be a low molecular weight compound such as ethyleneglycol monoallylether {2-(aryloxy)ethanol}, or a high molecular weight compound such as $C_3H_5$—O—$(C_2H_4O)_{10}$—H, $C_3H_5$—O—$(C_2H_4O)_{22}$$(C_3H_6O)_{22}$—$C_4H_5$, $C_{11}H_{21}$—O—$(C_2H_4O)_{21}(C_3H_6O)_7$—H.

The glycerine compound may be a monoglycerine or a polyglycerine such as a diglycerine or triglycerine, and their alkyl esters. Specifically, the following structures can be used: $C_3H_5$—O—$CH_2CH(OH)CH_2OH$, $C_3H_5$—O—$(CH_2CH(CH_2OH)O)_2H$, $C_3H_5$—O—$CH_2CH(OH)CH_2O$$(CH_2CH(CH_2OH)O)_2H$, $C_3H_5$—O—$CH_2(CH_2OCH_2CH(OH)CH_2OH)_2$ The alkenylated sugar may be an allylated derivative of a monosaccharide such as alpha-allylglycoside, beta-glucoside or a mixture thereof, an allylated derivative of a disaccharide or a polysaccharide, or a mixture thereof.

Here, the organohydrogen polysiloxane may be straight chain, branched or cyclic, but in order to make the addition reaction go smoothly, it is preferred that it is mainly straight chain.

The blending proportion of the sum total of the organic compound represented by the organohydrogen polysiloxane, the polyoxyalkylene compound, glycerin compound, sugar compound, alkylenated compound, and/or the organic compound having the above-mentioned general formula (5), is 0.5–2.0, but preferably 0.8–1.2 in terms of the mole ratio of SiH groups and terminal unsaturated groups.

It is desirable to perform the above-mentioned addition reaction in the presence of a platinum catalyst or rhodium catalyst. Specifically, platinum hydrochloride, alcohol-modified platinum hydrochloride and platinum hydrochloride-vinyl siloxane complex may conveniently be used. The amount of catalyst used can be the actual amount of catalyst, but in terms of the amount of platinum or rhodium, it is 50 ppm or less and preferably 20 ppm or less.

The above-mentioned addition reaction may be performed in an organic solvent if required.

As organic solvent, aliphatic alcohols such as methanol, ethanol, 2-propanol and butanol, aromatic hydrocarbons such as toluene and xylene, aliphatic or alicyclic hydrocarbons such as n-pentane, n-hexane or cyclohexane and halogenated hydrocarbons such as dichloromethane, chloroform and carbon tetrachloride may be mentioned, but for use in cosmetics, ethanol and 2-propanol (isopropyl alcohol) are suitable.

There is no particular limitation on the addition conditions, but the reaction may conveniently be performed under reflux for 1 to 10 hours. As post-treatment, in order to make SiH react completely or to eliminate SiH completely, a compound which has double bonds, such as 1-hexane, is made to react with the remaining SiH. Alternatively, an alkaline substance such as caustic soda, is added to dehydrate the SiH.

In the above process, when the addition reaction is performed in the presence of a platinum catalyst, an internal shift of the terminal double bond of the above-mentioned alkylene compound occurs. For example, in terminal allyl etherated polyoxyalkylene, propenyl etherated polyoxyalkylene (propenyl etherated polyether) is produced.

As the normal addition reaction and the isomerization reaction of polyoxyalkylene occur simultaneously even if the quantity of the hydrogen siloxane used exceeds the quantity which naturally reacts with terminal double bond-containing polyoxyalkylene, the production of polyether which isomerizes and contains an internal double bond is unavoidable. Moreover, from silicone chemistry research, it is known that internal double bond-containing polyether does not react with hydrogen siloxane, but remains in the system.

Due to this, in conventional polyether-modified silicones synthesized in the presence of a platinum catalyst, a terminal and internal double bond containing polyether will definitely remain, and the degree of unsaturation of the whole system was also 0.02 or higher.

However, due to oxidizative degradation of the polyether, the solution of polyether-modified silicone tends to become more acidic with time.

Therefore, when the polyether-modified silicone is blended with a cosmetic material in an aqueous system, decomposition of propenyl etherated polyether proceeds gradually in a solution of pH 7 or less, and propionaldehyde is produced, causing a foul odor.

Because of the foul odor produced with time, polyether modified silicone could not be mixed in large amounts with hair treatment, skin care and makeup, and particularly in a skin care or makeup material used close to the nose.

Thus, by performing hydrogen addition to eliminate unsaturated groups, the amount of propionaldehyde which was produced could be decreased and a certain amount of de-odorizing was possible.

However, as part of the aldehyde condensed to an aldehyde condensation product, it remained in the system as it was even if the above-mentioned treatment was performed, so the foul odor due to decomposition of the aldehyde compound could not be eliminated. In the acid treatment, this aldehyde condensation product could be decomposed, but as there was a limit to how far the unsaturated groups could be eliminated, the foul smell of the resulting aldehyde could not be completely removed.

In order to resolve this inconvenience, in this invention, the aldehyde condensation product which remains in the silicone is decomposed by performing a hydrogen addition reaction on the reaction solution after the addition reaction to hydrogenated unsaturated bonds, and by using a solution of pH 7 or less containing an acidic substance such as a mineral acid, organic acid or Lewis acid, preferably with heat treatment.

In this invention, the above problem can be solved also by hydrogenating the aldehyde and the alkenylated ether compound which were produced by the hydrogen addition reaction after decomposing the propenyl etherated polyether in the reaction solution from the addition reaction, using an aqueous solution of pH 7 or less containing an acidic substance such as a mineral acid, organic acid or Lewis acid as reagent. However, as there is a limit to removing the aldehyde condensation product completely in this case, the useful amount of modified silicone compound was limited.

The purified silicone thus obtained contains almost no polyether having double bonds which existed in the polyether-modified silicone before treatment, and the degree (meq/g) of unsaturation of the whole polyether modified silicone can be arranged to be 0.002 or less, or 0.001 or less.

Therefore, the amount of aldehyde and ketone generated in 0.23N hydrochloric acid even during aging at 50° C. for 0.5 hours, can be arranged to be 100 ppm or less, or 70 ppm or less, of the polyether modified silicone.

In this invention, mineral acids, organic acids and Lewis acids can be used as the acid in the treatment reagent.

Examples of mineral acids are hydrochloric acid, sulfuric acid, nitric acid, carbonic acid and phosphoric acid.

Examples of organic acids are carboxylic acids such as formic acid, acetic acid and trifluoroacetic acid, sulfonic acid, sulfenic acid, phenol acid, and primary and secondary nitroglycerine compounds.

Examples of Lewis acids are $AlCl_3$, $FeCl_3$, $TiCl_4$, $BF_3$, and $Et_2O$. These acids are used in a combined system with water, and when it is necessary to remove the acid, it is preferred to use an acid of low boiling point such as hydrochloric acid, formic acid, acetic acid or trifluoroacetic acid.

Moreover, from the viewpoint of efficiency, it is desirable to use hydrochloric acid or trifluoroacetic acid which are strong acids.

In measuring the amount of aldehyde which remains by HPLC (high-speed liquid chromatography) or carbonyl value, in order to characterize the carbonyl groups by 2,4-DNPH (2,4-dinitrophenylhydrazine) and to perform UV measurement, the most desirable acid is hydrochloric acid due to the necessity of decreasing the disturbing molecule as much as possible. In general, it is desirable to use the acid together with water rather than the acid alone, and to heat to a temperature below the boiling point of water. Due to this treatment, decomposition of the internal double bond containing polyether proceeds rapidly, and aldehyde condensation products also decompose. For example, when using hydrochloric acid as the processing agent, a hydrogen chloride concentration of $10^{-4}N$ is sufficient, and the pH of the hydrochloric acid is then 4.0. Further, if $10^{-3}N$ hydrochloric acid is used to increase the decomposition reaction rate, when this is about 10 wt %' relative to a polyether-modified silicone which uses, for example, allyl etherated polyether as starting material, the decomposition reaction completes in several hours. Consequently, internal double bond containing polyethers like propenyl etherated polyether disappear almost completely, and the majority of the aldehyde condensation products are decomposed.

As for the treatment temperature, it is desirable to carry out the reaction at 80° C. or less to prevent oxidation of the hydrophilic group. The addition amount of aqueous solution is preferably 0.1–100%, and more preferably 5–30%, of the weight of modified silicone.

In this invention, hydrochloric acid may for example be added and a hydrolysis reaction performed on the modified silicone after solvent removal. Further, production of the aldehydes and ketones which cause the foul odor may be forced by adding hydrochloric acid to the reaction solution after the addition reaction of hydrogen siloxane and terminal double bond-containing polyether using a platinum catalyst. These may be removed together with the hydrochloric acid and the solvent. From the viewpoint of productivity, the latter method wherein an aqueous solution is added to the reaction liquor to give a solution of pH 7 or less, and heating and stirring, is the most desirable.

Strip refining may be performed under normal pressure or reduced pressure, and the temperature is 120° C. or less. In order to carry out strip refining efficiently under this temperature condition, it is desirable to perform the reaction under reduced pressure, or if not, perform it at ordinary pressure in a current of an inert gas.

Even using the above-mentioned acid solution, it is difficult to eliminate the odor. Specifically, as there is a difference in the rate of hydrolysis of alkenyl ether and propenyl ether by the acid solution, alkenyl ether remains. In order to prevent this problem, it is necessary to carry out hydrogen addition on the solution after the addition reaction or the solution after acid treatment.

As a hydrogen addition reaction, there is the hydrogen method and the metal hydride method. Further, there is a uniform reaction and an non-uniform reaction. Although these can also be performed independently, they can also be carried out together. However, considering the advantage that the used catalyst does not remain in the product, the non-uniform contact hydrogen addition reaction using a solid catalyst is to be preferred.

Examples of solid catalysts are simple substances or compounds of nickel, palladium, platinum, rhodium, cobalt, chromium, copper and iron. In this case, there need not be a catalyst carrier, but if used, examples are activated carbon, silica, silica alumina, alumina, zeolite, etc. These catalysts can be used independently, but also in combination. The most preferred catalyst is Raney nickel, which is also the most economical. As Raney nickel is usually produced and used in alkali, it is necessary to measure the pH of the reaction solution carefully. Moreover, as the reaction system is weakly alkaline, hydrolysis by an acid solution is effective for deodorization.

In general, it is desirable to perform the hydrogen addition reaction at 1–100 MPa and 50–200° C. The hydrogen addition reaction may be performed in fractions or continuously. In the case of fractions, the reaction time depends on the amount of catalyst, temperature, etc., but it is generally 3–12 hours. Although the hydrogen pressure can be suitably adjusted to a fixed pressure, the terminal point of the hydrogen addition reaction can be determined, by carefully observing a pressure gauge, as the point where the hydrogen pressure does not change.

After the hydrogen addition reaction, a copolymer can be obtained by filtering the reaction solution and distilling off the solvent. The amount of aldehyde in the modified silicone compound of this invention purified by performing such hydrogen addition treatment and acid treatment can be set to 70 ppm, 20 ppm or less or 10 ppm or less.

As polyether-modified silicone absorbs the oxygen in air like the oil and fats in cosmetics, it gradually deteriorates due to auto-oxidation, and causes acidification.

Acidification leads to the odor of aldehydes such as acetaldehyde, and of acids such as acetic acid, therefore it causes a foul odor. Stability to oxidization can be increased using additives which suppress oxidation such as phenol, hydroquinone, benzoquinone, aromatic amines and vitamins. Examples of such antioxidation agents are BHT (dibutylhydroxytoluene) and vitamin E (d-delta-tocopherol).

Vitamin E is desirable for use in cosmetics, and particularly skin care products. It is preferred that the addition amount of antioxidant is 10–500 ppm, and preferably 50–300 ppm, relative to the polyether-modified silicone.

Although the silicone compound of this invention can be used for various purposes, it is suitable for all cosmetics applied externally, and especially for the skin and hair.

In this case, the blending amount of the silicone compound of the above-mentioned formula (1) is 0.1–40% of the total weight of the cosmetic materials.

Components usually used for cosmetic materials may also be used in the cosmetic material of this invention to the extent that they do not interfere with the effect of this invention.

Examples are water, powders, alcohol, water-soluble high polymers, coating agents, oils, oil-soluble gelating agents, organic modified argillite, surfactants, resin, ultraviolet-ray absorbents, moisturizers, antiseptics, antibacterial agents, spices, salts, antioxidizing agents, pH adjusting agents, chelating agents, cooling agents, anti-inflammatory agents, ingredients for lustrous skin (whitening agents, cell rejuvenating agents, dry and rough skin improving agents, blood circulation promoters, skin astringents, anti-seborrheic agents etc.), vitamins, aminoacids, nucleic acids, hormones and clathrates.

There is no particular limitation on powders if used for usual cosmetic materials, both as regards the form (spherical, acicular, tabular), particle diameter (smoke, particulates, paints) and particle structure (porosity, non-porous), for example, inorganic powders, organic powders, surfactant metal salt powders, colored pigments, pearl pigments, metal powder pigments and natural coloring matter. Specific examples of inorganic powders are titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, red mica, black mica, lichia? mica, silicic acid, anhydrous silicic acid, aluminum silicate, magnesium silicate, magnesium silicate, calcium silicate, barium silicate, strontium silicate, metal tungstates, hydroxyapatite, vermiculite, haidilite, bentonite, monmorillonite, hectorite, zeolite, ceramic powder, secondary calcium phosphate, alumina, aluminum hydroxide, boron nitride, boron nitride and silica.

Examples of organic powders are polyamide powders, polyester powders, polyethylene powders, polypropylene powders, polystyrene powders, polyurethane, benzoguanamine powder, polymethylbenzoguanamine powder, tetrafluoroethylene powder, polymethylmethacrylate powder, cellulose, silk powder, Nylon powder, 12 nylon, 6 nylon, silicone powder, styrene-acrylic acid copolymer, divinylbenzene styrene copolymer, vinyl resin, urea resin, phenol resin, fluororesin, silicone resin, acrylic resin, melamine resin, epoxy resin, polycarbonate resin, microcrystalline fiber powder, starch powder and lauryl lysine.

Examples of surfactant metal salt powders (metal soaps) are zinc stearate, aluminum stearate, calcium stearate, magnesium stearate, zinc myristinate, magnesium myristinate, zinc cetyl phosphate, calcium cetyl phosphate and zinc sodium cetyl phosphate; examples of colored pigments are inorganic red pigments such as iron oxide, iron hydroxide and titanium oxide, inorganic brown pigments such as gamma-iron oxide, inorganic yellow pigments such as yellow iron oxide and ocher, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as Prussian blue and ultramarine blue, lakes of tar pigments, lakes of natural dyes, and synthetic resin powders which are composites of these powders.

Examples of pearl pigments are titanium oxide-coated mica, titanium oxide-coated mica, bismuth oxychloride, titanium oxide-coated bismuth oxychloride, titanium oxide-coated talc, scales foil and titanium oxide-coated colored mica.

Examples of metal powder pigments are aluminum powder, copper powder and stainless steel powder.

Examples of tar colorants are red No. 3, red No. 104, red No. 106, red No. 201, red No. 202, red No. 204, red No. 205, red No. 220, red No. 226, red No. 227, red No. 228, red No. 230, red No. 401, red No. 505, yellow No. 4, yellow No. 5, yellow No. 202, yellow No. 203, yellow No. 204, yellow No. 401, blue No. 1, blue No. 2, blue No. 201, blue No. 404, green No. 3, green No. 201, green No. 204, green No. 205, orange No. 201, orange No. 203, orange No. 204, orange No. 206 and orange No. 207.

Examples of natural colorants are carminic acid, laccaic acid, carthamin, bradilin and crocin.

These powders may be combined in a range which does not interfere with the effect of this invention, or may be processed with common oils and silicone oil, fluorine compounds or surfactants, and two or more types can also be used.

Examples of alcohols are lower alcohols such as ethanol and isopropanol, and sugar alcohols such as sorbitol and maltose.

Examples of sterols are cholesterol, mitosterol, phitosterol and lanosterol.

Examples of water-soluble polymers are vegetable high polymers such as gum arabic, tragacanth, galactan, carob gum, guar gum, karaya gum, carrageenan, pectin, agar, quince seed, and starch (rice and corn), potato, wheat, algae colloid, tranto gum and locust bean gum, microbial polymers such as xanthan gum, dextran, succinoglucan, and pullulan, animal polymers such as collagen, casein, albumin and gelatin, starch polymers such as carboxymethyl starch and methyl hydroxypropyl starch, cellulose polymers such as methyl cellulose, ethyl cellulose, methyl hydroxypropyl cellulose, carboxymethyl cellulose, hydroxymethyl cellulose, hydroxypropyl cellulose, nitroglycerine cellulose, cellulose sodium sulfate, sodium carboxymethyl cellulose, crystalline cellulose and cellulose powder, alginic acid polymers such as sodium alginate and alginic acid propylene glycol ester, vinyl polymers such as polyvinyl methyl ether and carboxyvinyl polymer, polyoxyethylene polymer, polyoxypropylene copolymer polymer, acrylic polymers such as polyethylacrylate and polyacrylamide, polyethylene imine, inorganic water-soluble polymers such as bentonite, magnesium aluminum silicate, montmorillonite, bedellite, nontronite, saponite, hectorite and silicic acid anhydride.

In addition, a coating agent such as polyvinyl alcohol and polyvinylpyrrolidone may be included.

Any oils usually used in cosmetic materials may be used, and it may be solid, semisolid or liquid. Examples are semisynthetic animal and vegetable oils such as avocado oil, linseed oil, almond oil, Chinese wax, perilla oil, olive oil, cacao butter, kapok wax, kaya oil, carnauba wax, liver oil, candellila wax, beef tallow, beef leg fat, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, squalene, shellac wax, turtle oil, soybean oil, tea seed oil, camellia oil, evening primrose oil, corn oil, lard, rape seed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cotton seed oil, cotton wax, Japan wax, haze kernel oil, montan wax, coconut oil, hydrogenated coconut oil, tricoconut oil fatty acid glyceride, mutton tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether and egg yolk oil.

Examples of hydrocarbon oil are ozokerite, squalane, squalene, ceresin, paraffin, paraffin wax, liquid paraffin, pristane, polyisobutylene, microcrystalline wax and vaseline.

Examples of higher fatty acids are lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of higher alcohols are lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, mono stearyl glycerin ether (batyl alcohol) and monooleyl glyceryl ether (cerakyl alcohol).

Examples of ester oils are diisobutyl ester adipate, 2-hexyl decyl adipate, di-2-heptyl undecyl adipate, N-alkyl glycol monoisostearate, isocetyl isostearate, trimethylolpropane triisostearate, di-2-ethylhexane acid ethylene glycol, 2-ethylhexane acid cetyl, tri-2-ethylhexane acid trimethylolpropane, tetra-2-ethylhexane acid pentaerythritol, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyl decyl palmitate, 2-heptyl undecyl palmitate, 12-hydroxy stearyl acid cholesteryl, dipentaerythrytol fatty acid ester, isopropyl myristate, octyldodecyl myristate, 2-hexyl decyl myristate, myristyl myristate, dimethyl octanoic acid hexyl decyl, ethyl laurate, hexyl laurate, N-lauroyl-L-glutaminic acid 2-octyldodecyl ester and diisostearyl malate.

Examples of glyceride oils are aceto glyceryl. triisooctanoic acid glyceride, triisostearic acid glyceride, triisopalmitic acid glyceride, monostearic acid glyceride, di-2-heptyl undecanoic acid glyceride, trimyristic acid glyceride and myristic acid isostearic acid diglyceride.

Examples of silicone oils are low viscosity to high viscosity organopolysiloxanes such as methylphenylpolysiloxane, methylhydrogenpolysiloxane and dimethylsiloxane methylphenylsiloxane copolymer, cyclic siloxanes such as decamethyl cyclopentasiloxane, dodecamethylcyclohexasiloxane, tetramethyltetrahydrogencyclotetrasiloxane and tetramethyltetraphenylcyclotetrasiloxane, silicone rubbers such as gummy dimethylsiloxane methylphenylsiloxane copolymer and cyclic siloxane solutions of silicone rubber, trimethylsiloxysilicic acid, cyclosiloxane solutions of trimethylsiloxy silicic acid and higher alkoxy-modified silicones such as stearoxysilicone, higher fatty acid-modified silicones, alkyl-modified silicones, amino-modified silicones, fluorine-modified silicones, and silicone resins. Examples of fluorine-containing oils are perfluoropolyether, perfluorodecaline and perfluorooctane, one, two or more of these oils being used as necessary.

Examples of oil-soluble gelatinizers, metallic soaps such as magnesium stearate and zinc myristate, aminoacid derivatives such as alpha-γ-di-n-butylamine, dextrin fatty acid esters such as dextrin stearic acid ester, dextrin 2-ethylhexaminic acid palmitic acid ester, sucrose fatty acid esters such as sucrose stearic acid ester, benzylidene derivatives of sorbitol such as dibenzylidine sorbitol, and organic compound-modified clay minerals such as dimethylbenzyldodecyl ammonium monmorillonite clay and dimethyldioctadecyl ammonium monmorillonite clay, one, two or more kinds being used as required.

The present cosmetic material, in addition to the above components, may contain known surfactants depending on the desired purposes. Such additional surfactants have no particular restrictions, but they may be any of anionic, cationic, nonionic and amphoteric ones so long as they have hitherto been used in general cosmetics.

Examples of a usable anionic surfactant include fatty acid soap, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides; sulfonates of formaldehyde condensate type; alkylsulfates; higher secondary alcohol sulfates; alkyl and aryl ether sulfates; fatty acid ether sulfates, fatty acid alkylolamide sulfates; ether sulfates, such as Turkey red oil; alkyl phosphates; ether phosphates; alkyl aryl ether phosphates; amide phosphates; and active agents of N-acylamino acid type.

Examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides; and examples of a usable amphoteric surfactant include betaine, aminocarboxylic acid salts and imdazoline derivatives.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane.

Examples of a moisture retention agent which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylate, polyoxyethylene glycoside, and polyoxypropylene methylglycoside.

Examples of an antiseptic agent which can be added include alkyl p-hydroxybenzoates, benzoic acid, sodium benzoate, sorbic acid, potassium sorbate and phenoxyethanol; and examples of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizers and phenoxyethanol.

Examples of an antioxidant which can be added include tocopherol, butylhydroxyanisole, dibutylhydroxytoluene and phytic acid; examples of a pH regulator which can be added include lactic acid, citric acid, glycolic acid, succinic acid, tartaric acid, dl-malic acid, potassium carbonate, sodium hydrogen carbonate and ammonium hydrogen carbonate; examples of a chelating agent which can be added include alanine, sodium ethylenediaminetetraacetate, sodium polyphosphate, sodium metaphosphate and phosphoric acid; examples of a refrigerant which can be added include L-menthol and camphor; and examples of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitizers, cholesterol derivatives and calf blood extract; rough dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and antiseborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an amino acid which can be added include glycine, valine, leucine, isoleucine, serine, threonine, phenylaranine, alginine, lysine, aspartic acid, glutamic acid, cystine, cysteine, methionine, and tryptophan; examples of a nucleic acid which can be added include deoxyribonucleic acid; and examples of hormone which can be added include estradiol and ethenyl estradiol.

The term "cosmetic materials" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse and treatment.

Additionally, the present cosmetic materials may have any form, including liquid, emulsion, solid, paste, gel and spray forms, if desired.

In the odorless modified silicone compound of this invention obtained as above, double bonds and aldehyde condensation products contained as impurities in the modified silicone are effectively decomposed, and ketones and aldehydes are removed. Therefore, even if combined with an aqueous system, it does not acquire an odor with time. Accordingly, it can be used also for cosmetic product applications which were not possible in the prior art.

EXAMPLES

This invention will now be explained in more detail by specific examples, although it is not to be construed as being limited thereby. In the following general formulae, M is the $Me_3SiO_{1/2}$ group, and D is the $Me_2SiO$ group. Units which modify the methyl groups in M and D by a substituent group will be referred to as $M^R$ and $D^R$. The "%" in the yields are "wt %".

Example 1

Polyether-Modified Polysiloxane 1

1450 g of a methylhydrogenpolysiloxane having a hydrogen gas generation amount of 14.0 ml/g and a weight average molecular weight of 5000, 475 g of polyoxyethylene (9) allyl ether and 500 g isopropanol were introduced in a glass reaction vessel, 0.2 g of 3%-platinic chloride/isopropanol solution were added, and an addition reaction was performed at 80° C. for five hours. The reaction liquor was transferred to an autoclave, 50 g of Raney nickel 50 g was added, hydrogen was introduced, and a hydrogenation reaction was performed at 100° C. for three hours. During the reaction, hydrogen pressure was maintained at 1 MPa.

The catalyst was filtered, 250 g of 0.005N/HCl aqueous solution was added, and hydrolysis was performed at 60° C.

for three hours. 2.5 g of 5% sodium bicarbonate water was added to neutralize. 0.39 g vitamin E was added to the reaction liquor, and distillation performed under reduced pressure (110° C./400 Pa). Subsequently, after filtering, 1960 g of polysiloxane oil having the general formula $M_2D_{60}D^{R*1}{}_3$, viscosity 880 mm²/s at 25° C. and specific gravity 1.009 was obtained. The yield was 80%.

$R^{*1}$: —$C_3H_6O(C_2H_4O)_9H$

Comparative Example 1

The hydrogenation reaction and hydrolysis of Example 1 were not performed. 0.39 g of vitamin E were added to the reaction liquor after the addition reaction of Example 1. Reduced pressure stripping was performed at 110° C./400 Pa. The filtered sample was labeled Comparison Sample 1.

Comparative Example 2

The hydrolysis of Example 1 was not performed. 0.39 g of vitamin E were added to the reaction liquor after the addition reaction of Example 1. Reduced pressure stripping was performed at 110° C./400 Pa. The filtered sample was labeled Comparison Sample 2.

Comparative Example 3

The hydrolysis of Example 1 was not performed. 250 g of 0.01N/HCl aqueous solution was added to the reaction solution after the addition reaction, and hydrolysis was performed at 70° C. for three hours. 5.0 g of 5%-sodium bicarbonate water was added to neutralize. 0.39 g of vitamin E was added to the reaction liquor, and reduced pressure stripping was performed at 110° C./400 Pa. The filtered sample was used as Comparison Sample 3.

The following was observed with the polysiloxane oils obtained in Example 1 and the Comparison Samples 1–3 obtained in the Comparative Examples.

Unsaturation (meq/g): Using heavy acetone as solvent, this was calculated from the ¹H signal of the unsaturated double bond hydrogen by ¹H-NMR. 5.1 ppm–5.3 ppm of d(2 H) was used for allyl groups and 6.1 ppm–6.3 ppm (1 H) was used for propenyl groups in the calculation.

Odor: 10 g of sample and 10 g of purified water were mixed, and observed after leaving at by 60° C. for 24 hours.

HPLC: 1 g of sample was dissolved in 10 ml special grade reagent ethanol, and used as the test liquid, and dissolved in 90 ml special grade ethanol containing 50 mg 2,4-DNPH. Subsequently, 2 ml hydrochloric acid was added, and purified water was added to make up to 50 ml [the concentration of hydrochloric acid in the reaction solution was then 1.44% (0.47N)]. 1.0 ml of the reaction liquor was added to 1.0 ml of the test solution [the concentration of hydrochloric acid in the reaction solution was then 0.72% (0.23N)]. The solution was warmed to 50° C. for 30 minutes, and HPLC was performed using $CH_3CN/H_2O$ (50/50) as eluant and UV of 365 nm.

The result is shown in the following table. ND means less than 0.001 meq/g.

|  | Example 1 | Comparative Example 1 | Comparative Example 2 | Comparative Example 3 |
|---|---|---|---|---|
| Degree of unsaturation meq/g | ND | 0.15 | ND | 0.001 |
| Odor | None | Strong aldehyde odor | Strong aldehyde odor | Acid odor |
| propionaldehyde ppm | less than 1 | 400 | 80 | less than 1 |
| Total aldehydeppm ppm | less than 1 | 440 | 120 | 130 |

Comparative Example 1 is a sample from which post-addition light fragments have been removed, the degree of unsaturation and aldehyde amount is high, and odor is strong.

On the other hand, in Comparative Example 2 where a hydrogenation reaction was performed, the degree of unsaturation decreases to the extent at which double bonds cannot be detected, but the generation amount of propionaldehyde is as high as 80 ppm. Accordingly, this propionaldehyde is not derived from unsaturated double bonds.

In Comparative Example 3, as compared with Example 1, highly concentrated hydrochloric acid was used and the degree of unsaturation was less than 0.002 meq/g. The generation amount of propionaldehyde is less than in Comparative Example 2 where hydrogenation was performed, but oxidation occurs due to heat-treatment by hydrochloric acid solution, causing odor. In U.S. Pat. No. 2,137,062, making the degree of unsaturation less than 0.002 meq/g is an important factor in controlling the process, but as seen from the above table, merely reducing the degree of unsaturation is not effective for reducing the total quantity of aldehyde.

In the treatment of the sample for HPLC measurement, as compared with the measurement condition of Ichinohe (aforesaid patent) ($10^{-4}$ N acid solution), a higher concentration of hydrochloric acid is used. Consequently, propionaldehyde can be considerably reduced, but other aldehydes and ketones are produced.

The above results show that, with hydrogenation treatment or acid treatment alone, removal of aldehyde and condensate in the reaction system is difficult, but deodoration can be achieved by performing both.

For the sample of Comparative Example 2, when ¹³C-NMR was measured using heavy acetone, a ¹³C signal which appears to be acetal was observed at 104 ppm. This signal was not observed with Example 1.

Example 2

Polyether-Modified Polysiloxane 2

600 g of a methylhydrogenpolysiloxane having a hydrogen gas generation amount of 93.0 ml/g and a weight average molecular weight of 1200, 1500 g of polyoxyethylene (12) allyl ether and 500 g ethyl alcohol were introduced in a glass reaction vessel, 0.2 g of 3%-platinic chloride/isopropanol solution were added, and an addition reaction was performed at 80° C. for five hours. 250 g of 0.005N/HCl aqueous solution was added, and hydrolysis was performed at 60° C. for three hours. 2.5 g of 5% sodium bicarbonate water was added to neutralize.

The reaction solution was transferred to an autoclave, 50 g of Raney nickel 50 g was added, hydrogen was introduced, and a hydrogenation reaction was performed at 100° C. for three hours. During the reaction, hydrogen pressure was maintained at 1 MPa. After filtering the catalyst, 0.42 g vitamin E was added to the reaction liquor, and distillation performed under reduced pressure (~110° C./400 Pa).

Thereby, 1660 g of polysiloxane oil having the general formula $M_2D_{10}D^{R*2}{}_5$, viscosity 130 mm$^2$/s at 25° C. and specific gravity 1.062 was obtained. The yield was 79%.

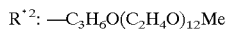
$R^{*2}$: —$C_3H_6O(C_2H_4O)_{12}Me$

Example 3

Polyether-Modified Polysiloxane 3

180 g of a methylhydrogenpolysiloxane having a hydrogen gas generation amount of 160 ml/g and a weight average molecular weight of 1800, 227 g of polyoxyethylene (9) allyl ether and 500 g isopropyl alcohol were introduced in a glass reaction vessel, 0.2 g of 3%-platinic chloride/isopropanol solution were added, and an addition reaction was performed at 80° C. for five hours.

390 g of polyoxypropylene (3) allyl oleyl ether (produced by Nippon Emulsion), RG-1252, was added, and the mixture heated under reflux for 3 hours.

10 g of 5% sodium hydroxide solution was added to hydrolyze unreacted Si—H groups, and 1.3 g concentrated hydrochloric acid was then added to neutralize. The reaction solution was transferred to an autoclave, 40 g of 5% Pd/C was added, hydrogen was introduced, and a hydrogenation reaction was performed at 100° C. for three hours. During the reaction, hydrogen pressure was maintained at 1 MPa.

After filtering the catalyst, 70 g of an 0.005N/HCl aqueous solution was added, and hydrolysis carried out at 60° C. for 3 hours. 0.7 g of 5% sodium bicarbonate solution was added to neutralize. 0.16 g vitamin E was added to the reaction liquor, and distillation performed under reduced pressure (~110° C./400 Pa). Thereby, 680 g of polysiloxane oil having the general formula $M_2D_{12}D^{R*1}{}_5D^{R*3}{}_8$, viscosity 390 mm$^2$/s at 25° C. and specific gravity 0.976 was obtained. The yield was 85%.

$R^{*3}$: —$C_3H_6O(C_3H_6O)_3C_{18}H_{37}$

Example 4

Polyether-Modified Polysiloxane 4

460 g of a methylhydrogenpolysiloxane having a hydrogen gas generation amount of 20.0 ml/g and a weight average molecular weight of 4600 (wherein, 5% of the total $Me_2SiO_{1/2}$ units is fluorine-modified methylhydrogenpolysiloxane which is a C $F_3C_2H_4MeSiO$ unit), 190 g of polyoxyethylene (9) allyl ether and 500 g isopropyl alcohol were introduced in a glass reaction vessel, 0.2 g of 3%-platinic chloride/isopropanol solution was added, and an addition reaction was performed at 80° C. for five hours.

The reaction solution was transferred to an autoclave, 25 g of 5% Pd/C was added, hydrogen was introduced, and a hydrogenation reaction was performed at 100° C. for three hours. During the reaction, hydrogen pressure was maintained at 1 MPa.

After filtering the catalyst, 70 g of 0.005N/HCl aqueous solution was added, and hydrolysis carried out at 60° C. for 3 hours. 0.16 g of 5% sodium bicarbonate solution was added to neutralize. 0.13 g vitamin E was added to the reaction liquor, and distillation performed under reduced pressure (~110° C./400 Pa). After filtration, 540 g of polysiloxane oil having the general formula $M_2D_{50}D^{C2H4C\ F3}{}_3D^{R*1}{}_4$, viscosity 860 mm$^2$/s at 25° C. and specific gravity 1.040 was obtained. The yield was 83%.

Example 5

Glycerine-Modified Polysiloxane 435 g of a methylhydrogenpolysiloxane having a hydrogen gas generation amount of 130 ml/g and a weight average molecular weight of 1200, 580 g of allyl glycerine ether and 500 g ethyl alcohol were introduced in a glass reaction vessel, 0.2 g of 3%-platinic chloride/isopropanol solution was added, and an addition reaction was performed at 80° C. for five hours. The reaction solution was transferred to an autoclave, 30 g of Raney nickel was added, hydrogen was introduced, and a hydrogenation reaction was performed at 100° C. for three hours. During the reaction, hydrogen pressure was maintained at 1 MPa.

After filtering the catalyst, 75 g of an 0.005N/HCl aqueous solution was added, and the reaction solution acid treated by heating at 60° C. for 3 hours. 0.8 g of 5% sodium bicarbonate solution was added to neutralize. Distillation was performed under reduced pressure (~110° C./400 Pa). Thereby, 792 g of polysiloxane oil having the general formula $M_2D_{11}D^{R*4}{}_7$, viscosity 86 mm$^2$/s at 25° C. and specific gravity 1.119 was obtained. The yield was 78%.

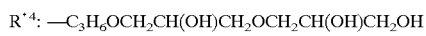
$R^{*4}$: —$C_3H_6OCH_2CH(OH)CH_2OCH_2CH(OH)CH_2OH$

Example 6

Sugar-Modified Polysiloxane 3

50 g of a methylhydrogenpolysiloxane having a hydrogen gas generation amount of 280 ml/g and a weight average molecular weight of 650, 300 g of allyl glucoside and 400 g ethyl alcohol were introduced in a glass reaction vessel, 0.2 g of 3%-platinic chloride/isopropanol solution was added, and an addition reaction was performed at 80° C. for five hours. The reaction solution was transferred to an autoclave, 25 g of Raney nickel was added, hydrogen was introduced, and a hydrogenation reaction was performed at 100° C. for three hours. During the reaction, hydrogen pressure was maintained at 1 MPa. After filtering the catalyst, 60 g of an 0.005N/HCl aqueous solution was added, and hydrolysis carried out at 60° C. for 3 hours. 0.6 g of 5% sodium bicarbonate solution was added to neutralize. Distillation was performed under reduced pressure (~110° C./400 Pa). Thereby, 298 g of polysiloxane having the general formula $M_2D^{R*5}{}_8$, a colorless powder with hygroscopic properties, was obtained. The yield was 85%.

$R^{*5}$:

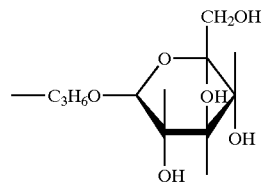

Below, the results of analysing the polysiloxanes in Examples 2–6 are shown. It is seen that in all cases, the amount of propionaldehyde falls to 10 ppm or less.

|  | Example 2 | Example 3 | Example 4 | Example 5 | Example 6 |
| --- | --- | --- | --- | --- | --- |
| Degree of unsaturation meq/g | ND | ND | ND | ND | ND |
| Odor | none | none | none | none | none |
| Propionaldehyde ppm | less than 1 | 5 | 3 | 9 | 5 |
| Total aldehyde ppm | 35 | 9 | 6 | 15 | 12 |

ND means less than 0.001 meq/g

Example 7

Lipstick

A lipstick comprising the following ingredients was prepared.

| (Ingredient) | (%) |
| --- | --- |
| 1. Palmitic acid/ethylhexane acid dextrin | 9.0 |
| 2. Glyceryl triisooctanoic acid | 22.0 |
| 3. Bentonite | 0.7 |
| 4. Modified silicone manufactured in Example 6 | 1.5 |
| 5. Modified silicone manufactured in Example 1 | 0.5 |
| 6. Decamethylcyclopentasiloxane | 40.0 |
| 7. 1,3-butylene glycol | 5.0 |
| 8. Purified water | 19.8 |
| 9. Color pigment | 1.5 |

(Manufacturing method)
A: Ingredient 1, part of ingredient 2 and ingredients 3–6 are mixed, and dissolved.
B: Ingredient 9 is mixed with the remainder of Ingredient 2, and dispersed by a roller.
C: B) is mixed with A) uniformly.
D: Ingredients 7, 8 are mixed, and heated
E: D) is added to C), and emulsified.

The lipstick obtained as above was a W/O type creamy lipstick having superior cosmetic durability. It spread well, and had no stickiness or oiliness.

Example 8

Eyeliner

An eyeliner comprising the following ingredients was prepared.

| (ingredient) | (%) |
| --- | --- |
| 1. Octamethylcyclotetrasiloxane | Residual quantity |
| 2. Modified silicone manufactured in Example 1 | 3.0 |
| 3. Silicone resin | 15.0 |
| 4. Dioctadecyldimethylammonium salt modified montmorillonite | 3.0 |
| 5. Siliconized black iron oxide | 10.0 |
| 6. 1,3-butylene glycol | 5.0 |
| 7. Preservative | Suitable amount |
| 8. Odorant | Suitable amount |
| 9. Purified water | 10 |

Silicone resin: 50%-D5 solution of silicone lattice compound for which [Me$_3$SiO$_{1/2}$]/[SiO$_2$] ratio is 0.8
Siliconized black iron oxide: 2% methylhydrogenpolysiloxane was added to black iron oxide, and heated
A: Ingredients 1–4 were mixed then ingredient 5 was added, mixed and dispersed uxiformly.
B: Ingredients 6–8 and 10 were mixed.
C: B was gradually added to A, emulsified, and ingredient 9 was added to obtain an eyeliner.

The eyeliner thus obtained is light, easily drawn, has a cool feeling and has no stickiness. There is no variation depending on temperature and time, and it is very stable in use. It has excellent water resistance and sweat resistance, and its cosmetic durability is very good.

Example 9

Eye Shadow

An eye shadow comprising the following ingredients was prepared.

| (Ingredient) | (%) |
| --- | --- |
| 1. Decamethyl cyclopentasiloxane | 15.0 |
| 2. Dimethyl polysiloxane (6cs) | 10.0 |
| 3. Modified silicone manufactured in Example 1 | 2.0 |
| 4. PEG (10) lauryl ether | 0.5 |
| 5. Siliconized chromium oxide (note 1) | 6.2 |
| 6. Siliconized ultramarine (note 1) | 4.0 |
| 7. Siliconized titanium clad mica (note 1) | 6.0 |
| 8. Sodium chloride | 2.0 |
| 9. Propylene glycol | 8.0 |
| 10. Preservative | Suitable amount |
| 11. Odoran | Suitable amount |
| 12. Purified water | Remainder |

(Note 1)
Siliconizing: 3% of methylhydrogenpolysiloxane is added to the powder, and the product is heat-treated
(Manufacturing method)
A: Ingredients 1–4 are mixed. Ingredients 5–7 are added, and dispersed uniformly.
B: Ingredients 8–10 and 12 are dissolved homogeneously.
C: B is gradually added to and emulsified with stirring, and ingredient 11 was added to obtain an eye shadow.

The eye shadow thus obtained spread lightly, had no oily or powdery feel, felt fresh and pleasant to use. In addition, it had good water resistance and repellency, lasted well, does not easily disintegrate, and has superior stability without variation due to temperature or time.

Example 10

Sun Tan Lotion

A sun tan lotion comprising the following ingredients was prepared.

| (Ingredients) | (%) |
| --- | --- |
| 1. Emulsifying agent composition (note 1) | 6.0 |
| 2. Dimethyl polysiloxane (20cs) | 49.0 |

-continued

| (Ingredients) | (%) |
|---|---|
| 3. 1,3-butylene glycol | 5.0 |
| 4. Sodium dehydroacetate | Suitable amount |
| 5. Oxidation inhibitor | Suitable amount |
| 6. Preservative | Suitable amount |
| 7. Odorant | Suitable amount |
| 8. Purified water | Remainder |
| a. Modified silicone manufactured in Example 1 | 10.0 weight parts |
| b. Dioctadecyldimethylammonium salt modified montmorillonite | 10.0 weight parts |
| c. Ethanol | 40.0 weight parts |

(note 1)
Emulsifying agent composition
(Manufacturing method)
A: Ingredient a is dissolved in ingredient c. Ingredient b is added.
B: After agitating A with a DESPER for one hour, ethanol is removed by an evaporator.
C: B is dried for one day and night at 50° C. to obtain the emulsifying agent composition of ingredient 1.
D: Ingredients 1 obtained in C and 2 are mixed.
E: Ingredients 3–6 and 8 are mixed uniformly.
F: E is gradually added to D and emulsified with stirring, and ingredient 7 is added to obtain an eye shadow.

The sun tan lotion thus obtained is fine, spread lightly, had no oily or powdery feel, felt fresh and pleasant to use. In addition, it had good water resistance and repellency, lasted well, does not easily disintegrate, and has superior stability without variation due to temperature or time.

Example 11

Suncut Cream

A sun cut cream comprising the following ingredients was prepared.

| (Ingredient) | (%) |
|---|---|
| 1. Decamethyl cyclopentasiloxane | 17.5 |
| 2. KP545 (note 1) | 12.0 |
| 3. Glyceryl triisooctanoate | 5.0 |
| 4. Octyl paramethoxycinnamate | 6.0 |
| 5. KSG21 (note 2) | 5.0 |
| 6. Modified silicone as manufactured in Example 1 | 1.0 |
| 7. Oil affinity treated zinc oxide | 20.0 |
| 8. Sodium chloride | 0.5 |
| 9. 1,3-butylene glycol | 2.0 |
| 10. Preservative | Suitable amount |
| 11. Odorant | Suitable amount |
| 12. Purified water | Residual quantity |

(note 1)
KP545: Acrylic silicone (manufactured by Shin-Etsu Chemical Co., Ltd.)
(note 2)
KSG21: Silicone gel (manufactured by Shin-Etsu Chemical Co., Ltd.)
(Manufacturing method)
A: Ingredient 2 is added to part of ingredient 1 uniformly, ingredient 7 is added, and dispersed by a bead mill.
B: The remainder of Ingredient 1 and Ingredients 3–6 are mixed, and blended uniformly.
C: Ingredients 8–10 and 12 are mixed, and dissolved.
D: C is added to B, and emulsified. A and Ingredient 11 are then added to obtain a sun cut cream.

The sun cut cream obtained above had no stickiness, spread lightly, had superior adhesion and compactness, good luster, cosmetics durability and very high stability with temperature and time.

Example 12

Foundation

A foundation comprising the following ingredients was prepared.

| (Ingredient) | (%) |
|---|---|
| 1. Decamethylcyclopentasiloxane | 45.0 |
| 2. Dimethylpolysiloxane (6cs) | 5.0 |
| 3. Modified silicone manufactured in Example 1 | 1.5 |
| 4. Modified silicone manufactured in Example 3 | 0.5 |
| 5. Octadecyl dimethylbenzyl ammonium salt modified montmorillonite | 4.0 |
| 6. Hydrophobically treated titania *1 | 10.0 |
| 7. Hydrophobically treated talc *1 | 6.0 |
| 8. Hydrophobically treated mica *1 | 6.0 |
| 9. Hydrophobically treated red ocher *1 | 1.6 |
| 10. Hydrophobically treated yellow iron oxide *1 | 0.7 |
| 11. Hydrophobically treated black iron oxide *1 | 0.2 |
| 12. Dipropylene glycol | 5.0 |
| 13. Para oxybenzoic acid methyl ester | 0.3 |
| 14. 2-amino-2-methyl-1,3-propanediol | 0.2 |
| 15. Hydrochloric acid | 0.1 |
| 16. Odorant | Suitable amount |
| 17. Water | Remainder |

*1: Hydrophobically treated; 2% methylhydrogenpolysiloxane is added to powder, and heat-treatment is performed
(Manufacturing method)
A: Ingredients 1–5 are mixed, and ingredients 6–11 are added and homogenized.
B: Ingredients 12–15 and 17 are heated, and dissolved. (pH of the water system is 9.0)
C: B is gradually added to A with stirring, emulsified and cooled. Ingredient 16 was added to obtain a foundation.

The foundation thus obtained was fine, spread lightly, had no stickiness or oiliness, and felt fresh and pleasant to use. In addition, it has excellent cosmetic durability, and has superior stability without variation due to temperature or time.

Example 13

Liquid Foundation

A liquid foundation comprising the following ingredients was prepared.

| (Ingredient) | (%) |
|---|---|
| 1. Decamethyl cyclopentasiloxane | 16.0 |
| 2. Dimethyl polysiloxane (6cs) | 8.0 |
| 3. Octyl paramethoxybenzalacetate | 3.0 |
| 4. 12-hydroxystearic acid | 1.0 |
| 5. Fluorine-modified silicone (note 1) | 15.0 |
| 6. Modified silicone manufactured in Example 4 | 5.0 |
| 7. Spherical silicone resin powder (note 2) | 3.0 |
| 8. Fluorine compound-treated particulate titania (note 3) | 8.0 |
| 9. Fluorine compound-treated mica titanium (note 3) | 1.0 |
| 10. Fluorine compound-treated titania (note 3) | 5.0 |
| 11. Fluorine compound-treated red ocher (note 3) | 0.9 |
| 12. Fluorine compound-treated yellow iron oxide (note 3) | 2.0 |
| 13. Fluorine compound-treated black iron oxide (note 3) | 1.0 |
| 14. Ethanol | 15.0 |
| 15. Glycerin | 3.0 |
| 16. Magnesium sulfate | 1.0 |
| 17. Preservative | Suitable amount |

-continued

| (Ingredient) | (%) |
|---|---|
| 18. Odorant | Suitable amount |
| 19. Purified water | Remainder |

(note 1)
Fluorine-modified silicone: FL-100 (Shin-Etsu Chemical Co., Ltd.)
(note 2)
Spherical silicone resin powder: KMP590 (Shin-Etsu Chemical Co., Ltd.)
(note 3)
Fluorine compound-treated: 5% coating with perfluoroalkyl ethyl phosphoric acid diethanolamine salt
(Manufacturing method)
A: Ingredients 7–13 are mixed uniformly.
B: Ingredients 1–6 are heated to 70° C. and mixed, then A is added to give a uniform dispersion.
C: Ingredients 14–17 and 19 were heated to 40° C., B was added gradually to emulsify, the mixture was cooled, and Ingredient 18 was added to give a liquid foundation.

The liquid foundation thus obtained spread lightly, and felt fresh and cool to use. In addition, it had excellent stability without variation due to temperature or time.

Example 14

Oil Foundation

An oil foundation comprising the following ingredients was prepared.

| (Ingredient) | (%) |
|---|---|
| 1. Amylum fatty acid ester | 6.0 |
| 2. Ceresin | 7.0 |
| 3. Polybutene | 4.0 |
| 4. Liquid paraffin | 34.0 |
| 5. Modified silicone manufactured in Example 5 | 6.0 |
| 6. Hydrophobically treated titania | 33.0 |
| 7. Hydrophobically treated mica titanium | 3.0 |
| 8. Pigment | 7.0 |
| 9. Odorant | Suitable amount |

Hydrophobically treated: 2% methylhydrogenpolysiloxane was added to powder, and heat-treated
(Manufacturing method)
A: Ingredients 1–5 are heated and mixed, and Ingredients 6–8 were added and blended homogeneously.
B: A was heated, and dissolved, Ingredient 9 is added, and the mixture was filled in a metal dish and cooled to obtain an oil foundation.

The oil foundation thus obtained was fine, spread lightly, had no stickiness or oiliness, and felt fresh and pleasant to use. In addition, it had excellent cosmetic durability, and has superior stability without variation due to temperature or time.

Example 15

Hair Cream

A hair cream comprising the following ingredients was prepared.

| (Ingredient) | (%) |
|---|---|
| 1. Decamethyl cyclopentasiloxane | 10.0 |
| 2. Methylphenyl polysiloxane | 5.0 |
| 3. Squalene | 4.0 |
| 4. Silicone resin | 1.0 |

-continued

| (Ingredient) | (%) |
|---|---|
| 5. Glyceryl dioleate | 2.0 |
| 6. Modified silicone manufactured in Example 1 | 4.0 |
| 7. Sorbitol sodium sulfate | 2.0 |
| 8. Sodium chondroitin sulfate | 1.0 |
| 9. Sodium hyaluronate | 0.5 |
| 10. Propylene glycol | 3.0 |
| 11. Preservative | 1.5 |
| 12. Vitamin E acetate | 0.1 |
| 13. Oxidation inhibitor | Suitable amount |
| 14. Odorant | Suitable amount |
| 15. Purified water | Remainder |

(Manufacturing method)
Silicone resin: 50%-D5 solution of silicone net-like compound in which $[Me_3SiO_{1/2}]/[SiO_2]$ ratio is 0.8
A: Ingredients 1 to 6, 11 and 12 are heated and mixed.
B: Ingredients 7 to 10 and 15 are heated and dissolved.
C: B was added gradually to A with stirring to make an emulsion. The emulsion was cooled, and then mixed with ingredient 14.

The hair cream spread smoothly, had neither tacky nor oily feel, and gave a moist, fresh and refreshing feel to the users' hair. Further, this hair cream kept its effect for a long time because of its good water resistance, water repellency and perspiration resistance, did not change with temperature and time, and had very high stability.

Example 16

Moisture-Retentive Cream

A moisture-retentive cream comprising the following ingredients was prepared.

| (Ingredient) | (%) |
|---|---|
| 1. Decamethylcyclopentasiloxane | 10.0 |
| 2. Methylphenylpolysiloxane | 3.0 |
| 3. Liquid paraffin | 5.0 |
| 4. Pentaerythrytol tetra-2-ethylhexanoate | 3.0 |
| 5. Cetyl 2-ethyl hexanoate | 5.0 |
| 6. Modified silicone manufactured in Example 1 | 1.0 |
| 7. Organopolysiloxane elastomer spherical powder (note 1) | 2.5 |
| 8. Hydrophobically treated silica (note 2) | 2.0 |
| 9. Zinc stearate | 2.0 |
| 10. Vitamin E acetate | 3.0 |
| 11. Polyethylene glycol 400 | 1.0 |
| 12. Sodium lactate | 1.0 |
| 13. 1,3-butylene glycol | 5.0 |
| 14. Preservative | Suitable amount |
| 15. Odorant | Suitable amount |
| 16. Purified water | Residual quantity |

(note 1)
Organopolysiloxane elastomer spherical powder: KMP594 (Shin-Etsu Chemical Co., Ltd.)
(note 2)
Hydrophobically-treated silica; Aerogel R 972 (Japan Aerogel)
(Manufacturing method)
A: Ingredients 1–6 and 9–10 are mixed uniformly. Ingredients 7 or 8 are added, and dispersed uniformly.
B: Ingredients 11–14 and 16 are added, and dissolved.
C: B is gradually added to A, emulsified and cooled. Ingredient 15 is added to obtain a moisture-retentive cream.

The moisture-retentive cream thus obtained spread lightly, felt fresh and pleasant to use and had no stickiness. In addition, it did not change due to temperature or time, was easy to use and highly stable.

Example 17

Hand Cream

A hand cream comprising the following ingredients was prepared.

| (Ingredient) | (%) |
|---|---|
| 1. Decamethyl cyclopentasiloxane | 30.0 |
| 2. Liquid paraffin | 10.0 |
| 3. Amino modified silicone gum (note 1) | 15.0 |
| 4. Modified silicone manufactured in Example 1 | 4.0 |
| 5. Distearyldimethylammonium chloride | 0.8 |
| 6. Vitamin E acetate | 0.1 |
| 7. Polyethylene glycol 4000 | 1.0 |
| 8. Glycerin | 10.0 |
| 9. Magnesium aluminum silicate | 1.2 |
| 10. Preservative | Suitable amount |
| 11. Odorant | Suitable amount |
| 12. Purified water | Remainder |

(note 1)
Amine equivalent 70000 g/mol
(Manufacturing method)
A: Ingredients 1 and 3 are heated, mixed and dissolved, and ingredients 2, 4–6 and 10 are heated and added.
B: Ingredients 7–9 and 12 are heated and mixed.
C: B is gradually added to A to emulsify, cooled, and ingredient 11 is added to obtain a hand cream.

The hand cream thus obtained had no tackiness, spread lightly, and had a cool feel.

It protected the skin effectively from washing in water, and had superior temperature stability.

Example 18

O/W Hand Cream

An O/W hand cream comprising the following ingredients was prepared.

| (Ingredient) | (%) |
|---|---|
| 1. KP545 (note 1) | 10.0 |
| 2. KP561 (note 2) | 8.0 |
| 3. Cetanol | 1.0 |
| 4. Glyceryl triisostearate | 5.0 |
| 5. Stearic acid | 3.0 |
| 6. Glyceryl monostearate | 1.5 |
| 7. Modified silicone manufactured in Example 1 | 0.7 |
| 8. Sesquioleic acid sorbitan | 0.5 |
| 9. Monooleic acid polyoxyethylene sorbitan | 1.0 |
| 10. Sodium hydroxide (1% aqueous solution) | 10.0 |
| 11. 1,3-butylene glycol | 5.0 |
| 12. Preservative | Suitable amount |
| 13. Odorant | Suitable amount |
| 14. Purified water | Remainder |

(note 1)
KP545: Acrylic silicone (Shin-Etsu Chemical Co., Ltd.)
(note 2)
KP561: Stearyl modified acrylic silicone (Shin-Etsu Chemical Co., Ltd.)
(Manufacturing method)
A: Ingredients 1–9 are mixed, heated and dissolved.
B: Ingredients 10–12 and 14 are mixed, and heated.
C: B is added to A to obtain an emulsion, cooled, and ingredient 13 is added to obtain a O/W hand cream.

The hand cream obtained above had no stickiness, spread lightly, had superior adhesion and compactness, good luster, cosmetics durability and very high stability with temperature and time.

Example 19

Emulsion

An emulsion comprising the following ingredients was prepared.

| (Ingredient) | (%) |
|---|---|
| 1. Decamethyl cyclopentasiloxane | 15.0 |
| 2. Methylphenyl polysiloxane | 5.0 |
| 3. Squalene | 5.0 |
| 4. Tetra-2-ethylhexane acid pentaerythritol | 5.0 |
| 5. Modified silicone manufactured in Example 1 | 3.0 |
| 6. Organo polysiloxane elastomer spherical powder (note 1) | 2.0 |
| 7. Hydrophobically-treated silica (note 2) | 0.5 |
| 8. Ascorbic acid magnesium phosphate | 1.0 |
| 9. Sodium chloride | 1.0 |
| 10. Polyethylene glycol 11000 | 1.0 |
| 11. Propylene glycol | 8.0 |
| 12. Preservative | Suitable amount |
| 13. Odorant | Suitable amount |
| 14. Purified water | Remainder |

(note 1)
Organo polysiloxane elastomer spherical powder: KMP594 (Shin-Etsu Chemical Co., Ltd.)
(note 2)
Hydrophobically-treated silica: Aerogel R 972 (Japan Aerogel)
(Manufacturing method)
A: Ingredients 1–5 are mixed uniformly, ingredients 6 and 7 are added, and dispersed uniformly.
B: Ingredients 8–10 are added to ingredient 14, and dissolved. Ingredients 11, 12 are homogenized, and added.
C: B is gradually added to A, emulsified and cooled. Ingredient 13 is then added to obtain an emulsion.

The emulsion obtained above spread lightly, and had no stickiness. It was easy to use, and had excellent stability with temperature and time.

Example 20

Beautifying Lotion

A beautifying lotion comprising the following ingredients was prepared.

| (Ingredient) | (%) |
|---|---|
| 1. Decamethyl cyclopentasiloxane | 12.0 |
| 2. Glyceryl triisooctanoate | 10.0 |
| 3. Modified silicone manufactured in Example 3 | 2.0 |
| 4. Modified silicone manufactured in Example 1 | 0.2 |
| 5. Glycerin | 10.0 |
| 6. Ascorbic acid magnesium phosphate salt | 3.0 |
| 7. Sodium chloride | 2.0 |
| 8. Preservative | Suitable amount |
| 9. Odorant | Suitable amount |

(Manufacturing method)
A: Ingredients 1–4 are heated and mixed.
B: Ingredients 5–8 and 10 are heated, and dissolved uniformly.
C: B is added gradually to A to emulsify, cooled, and ingredient 9 is added to obtain a beautifying lotion.

The beautifying lotion thus obtained is fine, spread lightly, had no tackiness, felt fresh and pleasant to use, and had superior stability without variation due to temperature or time.

Example 21

Antiperspirant

An antiperspirant comprising the following ingredients was prepared.

| (Ingredient) | (%) |
|---|---|
| 1. Octamethyl cyclopentasiloxane | 30.0 |
| 2. Modified silicone manufactured in Example 1 | 1.0 |
| 3. Monooleic acid polyoxyethylene sorbitan(20E. O.) | 0.5 |
| 4. Glycin salt of ruminium zirconium tetrachloride hydrate | 20.0 |
| 5. Purified water | Remainder |

(Manufacturing method)
A: Ingredients 1 and 2 are mixed.
B: ingredient 4 is dissolved in 5, and ingredient 3 is added.
C: B is gradually added to A, and emulsified to obtain an antiperspirant.

The antiperspirant obtained above spread lightly, had no tackiness or oiliness, did not become too white, had a clean feel in use, and very high stability with temperature and time

Example 22

Cleansing Cream

A cleansing cream comprising the following ingredients was prepared.

| (Ingredient) | (%) |
|---|---|
| 1. Dimethyl polysiloxane (6cs) | 5.0 |
| 2. Methylphenyl polysiloxane | 5.0 |
| 3. Liquid paraffin | 8.0 |
| 4. Jojoba oil | 2.0 |
| 5. Modified silicone manufactured in Example 1 | 2.5 |
| 6. Modified silicone manufactured in Example 3 | 0.5 |
| 7. Dextrin fatty acid ester | 0.8 |
| 8. Aluminum monostearate | 0.2 |
| 9. Aluminum chloride | 1.0 |
| 10. Glycerin | 10.0 |
| 11. Preservative | Suitable amount |
| 12. Odorant | Suitable amount |
| 13. Purified water | Remainder |

(Manufacturing method)
A: ingredients 1–8 are heated and mixed.
B: Ingredient 9–11 and 13 are heated, and dissolved.
C: B is gradually added to A with stirring to emulsify, cooled, and ingredient 12 is added to obtain a cleansing cream.

The cleansing cream thus obtained was fine, spread lightly, had no stickiness or oiliness, and felt fresh and pleasant to use. In addition, it had a good cleansing action, and had superior stability without variation due to temperature or time.

Example 23

Treatment Gel

A treatment gel comprising the following ingredients was prepared.

| (Ingredient) | (%) |
|---|---|
| 1. Ethanol | 20.0 |
| 2. Modified silicone manufactured in Example 2 | 0.5 |
| 3. Glyceryl triisooctanoate | 2.0 |
| 4. KSP-100 | 8.0 |
| 5. Carboxy vinyl powder (1% aqueous solution) | 20.0 |
| 6. Triethanolamine | 0.2 |
| 7. Purified water | 49.3 |

(Manufacturing method)
A: Ingredients 1–4 are mixed, and dispersed.
B: Ingredients 5–7 are mixed, and blended uniformly.
C: A is gradually added to B, and blended uniformly.

The treatment gel thus obtained spread lightly, had no stickiness or oiliness, and felt fresh and pleasant to use. In addition, it suited the skin, and had superior stability without variation due to temperature or time

Example 24

Washout Type Pack

A washout type pack comprising the following ingredients was prepared.

| (Ingredient) | (%) |
|---|---|
| 1. Dimethyl polysiloxane (6cs) | 3.0 |
| 2. Modified silicone manufactured in Example 1 | 2.0 |
| 3. Kaolin | 30.0 |
| 4. Carboxy vinyl polymer | 0.4 |
| 5. 1,3-butylene glycol | 10.0 |
| 6. Glycerin | 20.0 |
| 7. Preservative | Suitable amount |
| 8. Odorant | Suitable amount |
| 9. Purified water | Remainder |

(Manufacturing method)
A: Ingredients 1, 2 and 8 are mixed.
B: Ingredients 4–7 and 9 are mixed homogeneously, and ingredient 3 is blended with stirring.
C: A is added to B to emulsify, and a paste washout type pack was thus obtained.

The washout type pack thus obtained spread lightly in use, had excellent cleansing effect, and after washing out, left the skin feeling smooth without stickiness. It was very pleasant to use.

Example 25

Wipeoff Cleanser

A wipeoff cleanser comprising the following components was prepared.

| (Ingredient) | (%) |
|---|---|
| 1. Squalane | 10.0 |
| 2. Liquid paraffin | 28.0 |
| 3. Low density polyethylene | 2.0 |
| 4. Modified silicone manufactured in Example 1 | 2.0 |
| 5. Propylene glycol | 5.0 |
| 6. Oxidation inhibitor | Suitable amount |
| 7. Preservative | Suitable amount |
| 8. Odorant | Suitable amount |
| 9. Purified water | Remainder |

(Manufacturing method)
A: Ingredients 1–4 and 6–8 are mixed.
B: Ingredients 5 and 9 were heated and mixed, then added into A to emulsify while stirring to obtain a wipeoff cleanser.

The wipeoff cleanser thus obtained was not sticky in use, spread lightly, and had a moist feel. After wiping off, it left the skin moist without tackiness. It was very stable without change due to temperature or time.

Example 26

Deodorant

A deodorant comprising the following ingredients was prepared.

| (Ingredient) | (%) |
| --- | --- |
| 1. Decamethyl cyclopentasiloxane | 12.0 |
| 2. Dimethyl polysiloxane (6cs) | 4.0 |
| 3. Modified silicone manufactured in Example 1 | 1.0 |
| 4. Propylene glycol | 31.0 |
| 5. Triclosan | 0.1 |
| 6. Glycerin | 15.0 |
| 7. Preservative | Suitable amount |
| 8. Odorant | Suitable amount |
| 9. Purified water | Remainder |

(Manufacturing method)
A: Ingredients 1–3 are mixed.
B: Ingredient 5 is dissolved in 4, and ingredients 6–9 are mixed.
C: B is added to A while stirring vigorously to emulsify.
D: 65 parts C, and 35 parts of a propellant (n-butane, isobutane, propane mixture) were added to an aerosol can to obtain a deodorant.

The deodorant obtained as above did not drip even when used at high concentration. It was not sticky, and had a cool feel over time.

Example 27

Makeup Remover

A makeup remover comprising the following ingredients was prepared.

| (Ingredient) | (%) |
| --- | --- |
| 1. Modified silicone manufactured in Example 1 | 20.0 |
| 2. Polyoxyethylene (20) monostearic acid sorbitan | 10.0 |
| 3. Sorbitol | 10.0 |
| 4. Carrageenan | 0.5 |
| 5. Preservative | Suitable amount |
| 6. Odorant | Suitable amount |
| 7. Purified water | Remainder |

(Manufacturing method)
A: Ingredients 1–5 and 7 are added, and dissolved uniformly.
B: Ingredient 6 was added to A to obtain a makeup remover.

When a long-lasting foundation was removed using the makeup remover, it easily removed the foundation and sebum, easily removed dirt, spread easily in use, and left no stickiness with a clean feel. It was very easy and pleasant to use, and had excellent stability without any change due to temperature or time.

INDUSTRIAL APPLICABILITY

The modified silicone compound of this invention generates no odor even over time, and is therefore highly suitable for cosmetics. As the cosmetic material of this invention causes no odor even over time, it can be used safely, and as it is long-lasting, it is also economical. Also, the method of purifying the organopolysiloxane having a branch polymer comprising a hydrophilic group according to this invention requires no special technique or apparatus, which is particularly significant in industry.

What is claimed is:

1. A modified silicone compound, said compound being synthesized by performing an addition reaction between an organohydrogenpolysiloxane, and at least one compound chosen from an alkenylated polyoxyalkylene compound, an alkenylated glycerin compound and an alkenylated sugar in the presence of a platinum catalyst or rhodium catalyst to obtain a reaction liquor, and said compound being purified by decomposing aldehyde condensation products remaining in the resulting silicone compound by:

hydrogenating the reaction liquor from said addition reaction to hydrogenate unsaturated bonds, and treating with an aqueous solution of pH 7 or lower containing an acidic substance, or decomposing a propenyl etherated polyether in the reaction liquor from said addition reaction by treating with an aqueous solution of pH 7 or lower containing an acidic substance, and then hydrogenating the generated aldehydes and alkenylated ether compounds by hydrogenation, the degree of unsaturation (meq/g) in said modified silicone compound being 0.002 or less, and the generation amount of aldehydes when heat ageing is performed in 0.23N hydrochloric acid at 50° C. for 0.5 hours is 70 ppm or less of the modified silicone compound, thus producing a branched modified silicone compound.

2. The odorless modified silicone compound as defined in claim 1, wherein the purification of the modified silicone compound is performed by decomposing aldehyde condensation products remaining in the silicone, by hydrogenating the reaction liquor from said addition reaction to hydrogenate unsaturated bonds, and treating with an aqueous solution of pH 7 or lower containing an acidic substance.

3. The odorless modified silicone compound as defined in claim 1, wherein said modified silicone compound is represented by the following general formula (1):

$$R^1_a R^2_b SiO_{(4-a-b)/2} \quad (1)$$

wherein, $R^1$ in the formula is an alkyl group having 1–30 carbon atoms, aryl group, aralkyl group, fluorine-substituted alkyl group or an organic group represented by the general formula (2):

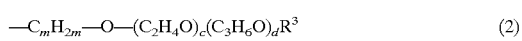

$$-C_m H_{2m}-O-(C_2H_4O)_c(C_3H_6O)_d R^3 \quad (2)$$

where $R^3$ is a hydrocarbon group having 5–30 carbon atoms, or an organic group represented by $R^4$—(CO)— where $R^4$ is a hydrocarbon group with 1–30 carbon atoms, c, d, and m are integers in the range $0 \leq c \leq 50$, $0 \leq d \leq 50$, and $0 \leq m \leq 15$, respectively, and $R^2$ is a hydrophilic group represented by the following general formula (3):

$$-Q-O-X \quad (3)$$

wherein, Q is a divalent hydrocarbon group with 3–20 carbon atoms which may contain at least one of an ether bond or ester bond, and X is a monovalent hydrophilic group derived from polyoxyalkylene, glycerin, and sugar; a and b are given by $1.0 \leq a \leq 2.5$ and $0.001 \leq b \leq 1.5$, respectively.

4. The odorless modified silicone compound as defined in claim 1, wherein the generation amount of aldehydes when said modified silicone compound is heat aged in 0.23N hydrochloric acid at 50° C. for 0.5 hours is 20 ppm or less.

5. The odorless modified silicone compound as defined in claim 3, wherein X is a monofunctional hydrophilic group comprising a polyoxyalkylene, and $R^2$ is represented by the following general formula (4):

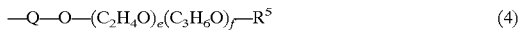  (4)

wherein, Q in the formula (4) is identical to Q in formula (3), $R^5$ is a hydrogen or a hydrocarbon group having 1–4 carbon atoms, e is an integer in the range 2–200, f is an integer in the range 0–200, e+f is 3–200 and e/f≧1.

6. The odorless modified silicone compound as defined in claim 3, wherein X is a monofunctional hydrophilic group comprising glycerine, and $R^2$ is a group chosen from the residues below

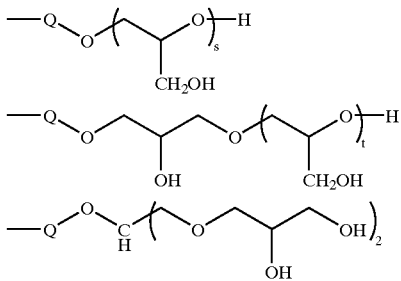

wherein, Q is identical to Q in formula (3), and s, t in the formula are integers in the range 1–20.

7. The odorless modified silicone compound as defined in claim 3, wherein X is a sugar residue, and $R^2$ is a monosaccharide or oligosaccharide.

8. A method of purifying a modified silicone compound, said compound being synthesized by performing an addition reaction between an organohydrogenpolysiloxane, and at least one compound chosen from an alkenylated polyoxyalkylene compound, an alkenylated glycerin compound and an alkenylated sugar in the presence of a platinum catalyst or rhodium catalyst to obtain a reaction liquor, said method comprising decomposition of aldehyde condensation products remaining in the resulting silicone compound by:

hydrogenating the remaining unsaturated bonds after hydrogenating the reaction liquor from said addition reaction, and treating with an aqueous solution of pH 7 or lower containing an acidic substance, or decomposition of a propenyl etherated polyether in the reaction liquor after said addition reaction by treating with an aqueous solution of pH 7 or lower containing an acidic substance, and then hydrogenating the generated aldehydes and alkenylated ether compounds by hydrogenation.

9. A cosmetic material comprising the odorless modified silicone compound as defined in claim 1.

10. The cosmetic material as defined in claim 9, comprising 10–500 ppm of an antioxidant relative to said odorless modified silicone compound.

11. A modified compound of formula (1):

  (1)

wherein, $R^1$ in the formula is an alkyl group having 1–30 carbon atoms, aryl group, aralkyl group, fluorine-substituted alkyl group or an organic group represented by the general formula (2):

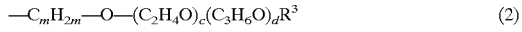  (2)

wherein $R^2$ is a hydrocarbon group having 5–30 carbon atoms, or an organic group represented by $R^{4-}(CO)-$ where $R^4$ is a hydrocarbon group with 1–30 carbon atoms, c, d, and m are integers in the range 0≦c≦50, 0≦d≦50, and 0≦m≦15, respectively, and $R^2$ is a group chosen from the residues below

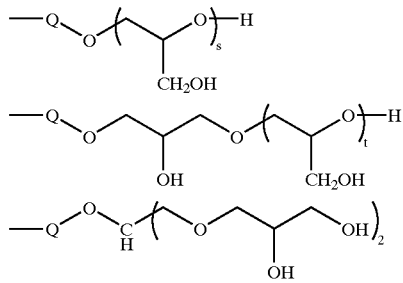

wherein, Q is a divalent hydrocarbon group with 3–20 carbon atoms which may contain at least one of an ether bond or ester bond, and s, t in the formula are integers in the range 1–20, said compound being synthesized by performing an addition reaction between an organohydrogenpolysiloxane, and at least one compound chosen from an alkenylated polyoxyalkylene compound, an alkenylated glycerin compound and an alkenylated sugar in the presence of a platinum catalyst or rhodium catalyst to obtain a reaction liquor, and the compound being purified by decomposing aldehyde condensation products remaining in the resulting silicone compound by:

hydrogenating the remaining unsaturated bonds after hydrogenating the reaction liquor from the addition reaction to hydrogenate unsaturated bonds, and treating with an aqueous solution of pH 7 or lower containing an acidic substance, or decomposing a propenyl etherated polyether in the reaction liquor from the addition reaction by treating with an aqueous solution of pH 7 or lower containing an acidic substance, and then hydrogenating the generated aldehydes and alkenylated ether compounds by hydrogenation, the degree of unsaturation (meq/g) in the modified silicone compound being 0.002 or less, and the generation amount of aldehydes when heat aging is performed in 0.23N hydrochloric acid at 50° C. for 0.5 hours in 70 ppm or less of the modified silicone compound.

12. A modified compound of formula (1):

  (1)

wherein, $R^1$ in the formula is an alkyl group having 1–30 carbon atoms, aryl group, aralkyl group, fluorine-substituted alkyl group or an organic group represented by the general formula (2):

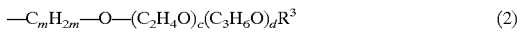  (2)

wherein $R^3$ is a hydrocarbon group having 5–30 carbon atoms, or an organic group represented by $R^{4-}(CO)-$ where $R^4$ is a hydrocarbon group with 1–30 carbon atoms, c, d, and m are integers in the range 0≦c≦50, 0≦d≦50, and 0≦m≦15 respectively, and $R^2$ is a monosaccharide or oligosaccharide and said compound being synthesized by performing an addition reaction between an organohydrogenpolysiloxane, and at least one compound chosen from an alkenylated polyoxyalkylene compound, an alkenylated glycerin compound and an alkenylated sugar in the presence of a platinum catalyst or rhodium catalyst to obtain a reaction liquor, and said compound being purified by decomposing aldehyde condensation products remaining in the resulting silicone compound by:

hydrogenating the remaining unsaturated bonds after hydrogenating the reaction liquor from the addition reaction to hydrogenate unsaturated bonds, and treating with an aqueous solution of pH 7 or lower containing an acidic substance, or decomposing a propenyl etherated polyether in the reaction liquor from the addition reaction by treating with an aqueous solution of pH 7 or lower containing an acidic substance, and then hydrogenating the generated aldehydes and alkenylated ether compounds by hydrogenation, the degree of unsaturation (meq/g) in the modified silicone compound being 0.002 or less, and the generation amount of aldehydes when heat ageing is performed in 0.23N hydrochloric acid at 50° C. for 0.5 hours in 70 ppm or less of the modified silicone compound.

13. A modified silicone compound according to claim 3, wherein X is a sugar residue.

14. A modified silicone compound according to claim 3, wherein X is a monofunctional hydrophilic group comprising glycerin.

15. The modified silicone compound as defined in claim 1, wherein the purification of the modified silicone compound is performed by decomposing a propenyl etherated polyether in the reaction liquor from said addition reaction by treating with an aqueous solution of pH 7 or lower containing an acidic substance, and then hydrogenating the generated aldehydes and alkenylated ether compounds by hydrogenation.

* * * * *